(12) United States Patent
Figueroa et al.

(10) Patent No.: US 6,336,932 B1
(45) Date of Patent: Jan. 8, 2002

(54) DEVICE FOR INSERTING A FLEXIBLE INTRAOCULAR LENS

(75) Inventors: Dennis Alexander Figueroa, Mission Viejo; Alok Nigam, Trabuco Cyn; Thomas Michael Heyman, Chino Hills; Henry W. Oviatt, Jr., Mission Viejo, all of CA (US)

(73) Assignee: Bausch & Lomb Surgical, Inc., Rochester, NY (US)

( * ) Notice: Subject to any disclaimer, the term of this patent is extended or adjusted under 35 U.S.C. 154(b) by 0 days.

(21) Appl. No.: 08/615,185

(22) PCT Filed: Aug. 7, 1995

(86) PCT No.: PCT/US95/09973

§ 371 Date: Jun. 25, 1996

§ 102(e) Date: Jun. 25, 1996

(87) PCT Pub. No.: WO96/03924

PCT Pub. Date: Feb. 15, 1996

Related U.S. Application Data

(63) Continuation-in-part of application No. 08/286,557, filed on Aug. 5, 1994, now abandoned.

(51) Int. Cl.[7] .................................................. A61F 9/00
(52) U.S. Cl. ...................................... 606/107; 623/6.43
(58) Field of Search ............................. 606/107; 623/4, 623/6, 6.11, 6.12, 6.38, 6.4, 6.42, 6.43, 6.44, 6.51, 6.54; 604/57, 59, 60

(56) References Cited

U.S. PATENT DOCUMENTS

| 1,876,703 A | * | 9/1932 | Lilly ............................ 604/59 |
| 2,761,446 A | * | 9/1956 | Reed ............................ 604/59 |
| 3,991,426 A | | 11/1976 | Flom et al. |
| 4,053,953 A | | 10/1977 | Flom et al. |
| 4,214,585 A | | 7/1980 | Bailey, Jr. |
| 4,244,370 A | | 1/1981 | Furlow et al. |
| 4,573,998 A | | 3/1986 | Mazzocco |
| 4,600,004 A | | 7/1986 | Lopez et al. |
| 4,681,102 A | | 7/1987 | Bartell |
| 4,699,140 A | | 10/1987 | Holmes et al. |
| 4,702,244 A | | 10/1987 | Mazzocco |
| 4,715,373 A | | 12/1987 | Mazzocco et al. |
| 4,747,404 A | | 5/1988 | Jampel et al. |
| 4,763,650 A | | 8/1988 | Hauser |
| 4,765,329 A | | 8/1988 | Cumming et al. |
| 4,822,360 A | | 4/1989 | Deacon |
| 4,834,094 A | | 5/1989 | Patton et al. |
| 4,836,201 A | * | 6/1989 | Patton et al. ................ 606/107 |
| 4,836,202 A | | 6/1989 | Krasner |
| 4,880,000 A | | 11/1989 | Holmes et al. |
| 4,919,130 A | | 4/1990 | Stoy et al. |
| 4,934,363 A | | 6/1990 | Smith et al. |
| 4,955,889 A | | 9/1990 | Van Gent |
| 4,957,505 A | | 9/1990 | McDonald |
| 4,976,716 A | | 12/1990 | Cumming |
| 5,007,913 A | | 4/1991 | Dulebohn et al. |
| 5,098,439 A | | 3/1992 | Hill et al. |
| 5,123,905 A | | 6/1992 | Kelman |
| 5,190,552 A | | 3/1993 | Kelman |

(List continued on next page.)

Primary Examiner—Glenn K. Dawson
(74) Attorney, Agent, or Firm—Fitzpatrick, Cella, Harper & Scinto

(57) ABSTRACT

An intraocular lens insertion device having a tubular member for receiving the lens and a plunger for pushing the lens into the eye. The lens is held in a suspended position by its haptics so that the optic portion of the lens does not contact the interior of the tubular member. The plunger tip is provided with a slot for holding the lens after it is expelled from the tubular member into the eye in order to alleviate the risks associated with uncontrolled unfolding of the lens or uncontrolled expulsion of the lens from the inserter into the eye.

31 Claims, 10 Drawing Sheets

U.S. PATENT DOCUMENTS

| | | |
|---|---|---|
| 5,242,450 A | 9/1993 | McDonald |
| 5,275,604 A * | 1/1994 | Rheinish et al. ............ 606/107 |
| 5,304,182 A * | 4/1994 | Rheinish et al. ............ 606/107 |
| 5,395,378 A | 3/1995 | McDonald |
| 5,494,484 A | 2/1996 | Feingold |
| 5,496,328 A | 3/1996 | Nakajima et al. |
| 5,499,987 A | 3/1996 | Feingold |
| 5,562,676 A * | 10/1996 | Brady et al. ................ 606/107 |
| 5,766,181 A * | 6/1998 | Chambers et al. .......... 606/107 |
| 5,873,879 A * | 2/1999 | Figueroa et al. ............ 606/107 |

* cited by examiner

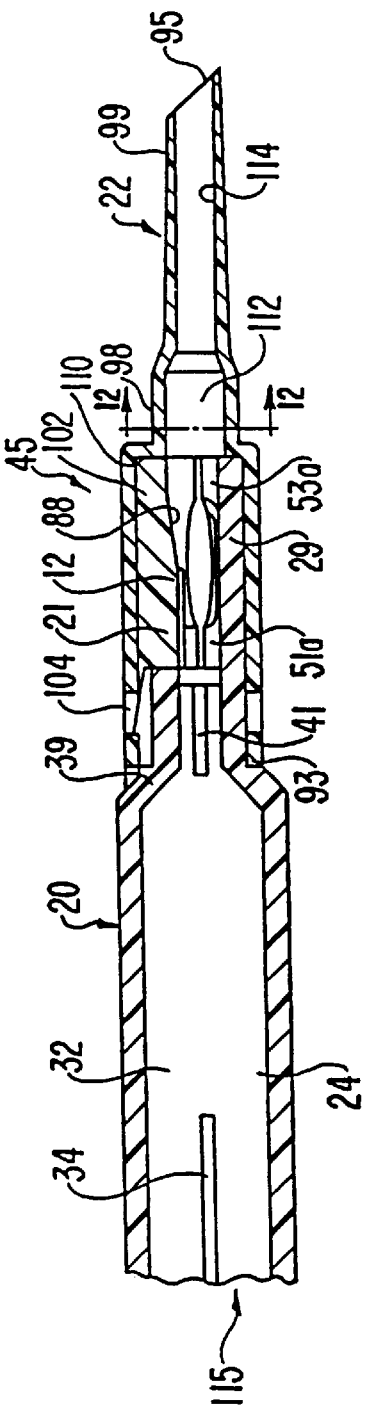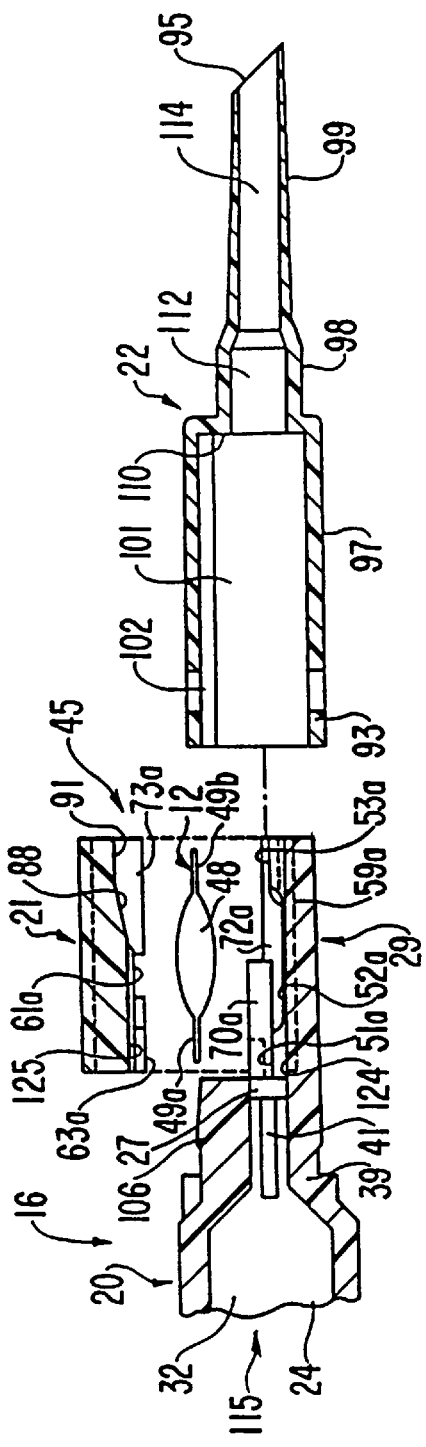

DEVICE FOR INSERTING A FLEXIBLE INTRAOCULAR LENS

This Appln is a 371 of PCT/US95/09973 filed Aug. 7, 1995 and a C-I-P of Ser. No. 08/286,557 filed Aug. 5, 1994, abn.

FIELD OF THE INVENTION

The present invention pertains to a device for inserting a flexible intraocular lens (IOL) into the eye of a patient.

BACKGROUND OF THE INVENTION

The natural crystalline lens of the eye plays a primary role in focusing light onto the retina for proper vision. However, the lens can become damaged due to injury or become cloudy because of the aging process or disease and form a cataract. To restore vision to the eye, the natural lens must be surgically removed and an artificial lens implanted as a replacement.

Many surgical procedures have been developed for removing the natural lens. As an example, phacoemulsification is one such process which has gained wide popularity. According to this procedure, a slender implement is inserted through an incision made in the eye and into the natural lens. The implement produces ultrasonic vibrations and emulsifies the lens. The emulsified portions of the lens are then aspirated out of the eye through a passage provided in the implement. As opposed to other procedures, this lens extraction method requires the surgeon to make only a narrow incision in the eye. In general, the use of a small incision can lessen the trauma and complications experienced during the surgery and postoperatively.

A flexible IOL comprises a central optic portion which focuses light on the retina and at least one outwardly extending haptic. Haptics can have a variety of different configurations, but most commonly are either a plate-like extension of the optic or loop shaped. In any event, the haptics extend outwardly to position the optic of the lens in alignment with the pupil. Flexible IOLs are particularly suited for insertion in the eye following a phacoemulsification lens extraction procedure. Whereas placement of a hard, non-foldable IOL would require widening of the small phacoemulsification incision, a flexible IOL can be compressed or folded for passage through the narrow incision in the eye. Once the lens is passed through the incision and released into the eye, it will expand to its original shape and size.

A number of different devices have been developed to implant a flexible IOL into an eye. See, for example, U.S. Pat. No. 4,573,998 to Mazzocco, U.S. Pat. No. 4,681,102 to Bartell, U.S. Pat. No. 4,919,130 to Stoy et al., and U.S. Pat. No. 5,275,604 to Rheinish et al. In general, these devices function to pass a compressed lens through the narrow incision made in the eye. These devices, however, require undue manipulation of the lens, include a multiplicity of parts, and/or fail to provide ample control of the lens as it enters the eye.

SUMMARY OF THE INVENTION

The present invention is a device which enables flexible IOLs to be easily folded, compressed and inserted through an incision in the eye. In general, the insertion device comprises a tubular member for receiving the lens and a plunger for pushing the lens through the tubular member and into the eye. As the lens is pushed through the passage it is compressed into a smaller configuration. The construction of the present invention ensures an easy, sure and consistent compression of the lens.

According to one aspect of the invention, the tubular member includes a staging area for holding the lens in an unstressed condition. The lens is preferably held in a suspended position by its haptics so that the optic remains substantially free of contact with the interior of the tubular member. In this manner, the device can be used as the lens package, and the device can be shipped and stored with the lens already in place and ready for use. As a result, unnecessary manipulation of the lens is avoided. According to another aspect of the invention, the plunger tip is provided with a structure which holds the lens to the plunger when the lens is pushed out of the tubular member. The distal tip of the plunger is preferably bifurcated to define a slot for partially receiving and gripping the lens. With this construction, the plunger is able to hold the lens when the lens exits the tubular member and expands into the eye. Holding the lens in this manner eases placement of the lens in the eye and alleviates the risks associated with uncontrolled unfolding of the lens or uncontrolled expulsion of the lens from the inserter into the eye.

BRIEF DESCRIPTION OF THE DRAWINGS

FIG. 13 is a partial cross sectional view taken along line 13—13 in FIG. 1, with an IOL in the staging area.

FIG. 14 is an exploded view of FIG. 13.

DETAILED DESCRIPTION OF THE PREFERRED EMBODIMENT

Figure 1:
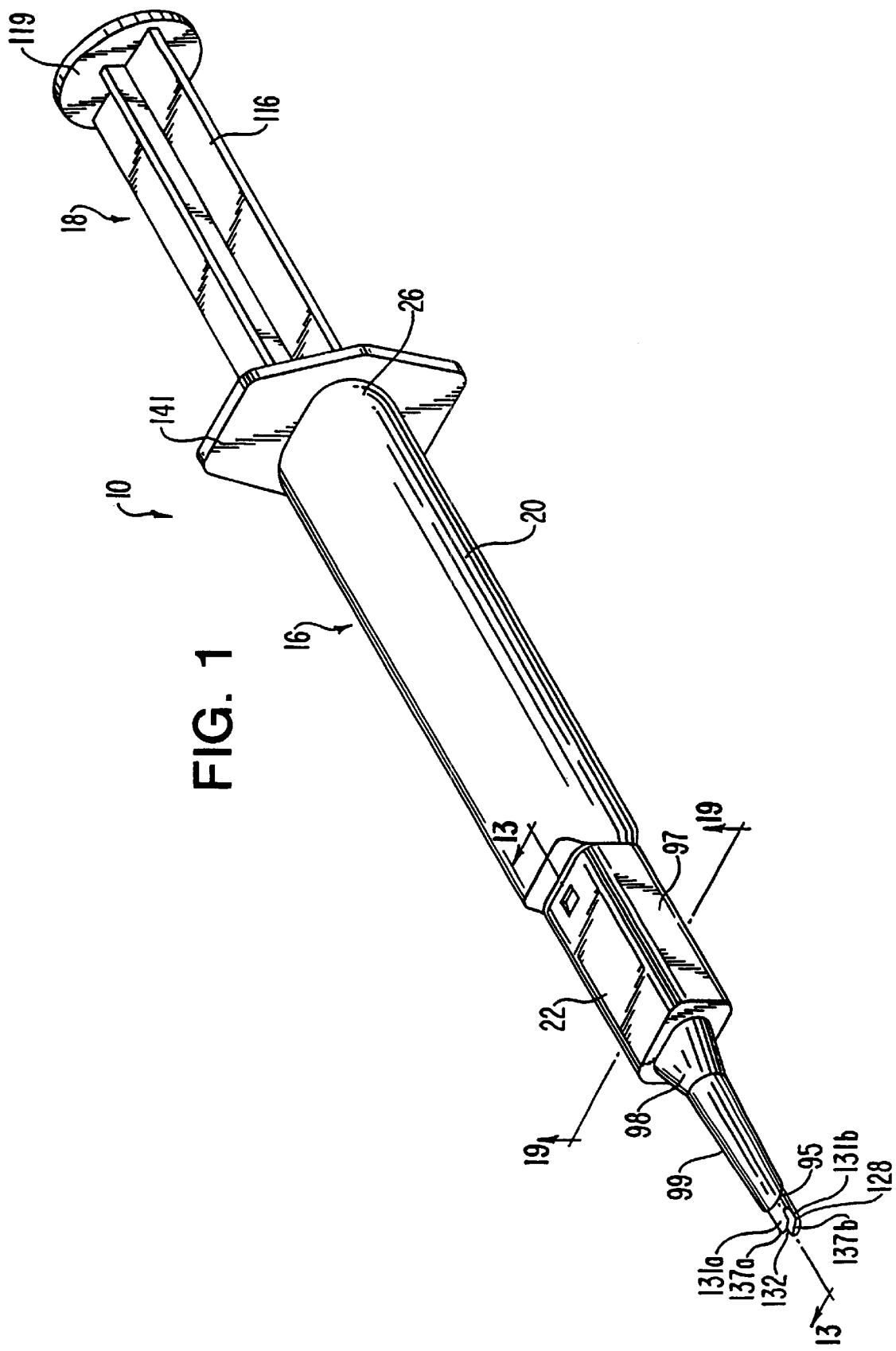
FIG. 1 is a perspective view of an insertion device in accordance with a preferred embodiment of the present invention.
Figure 26:
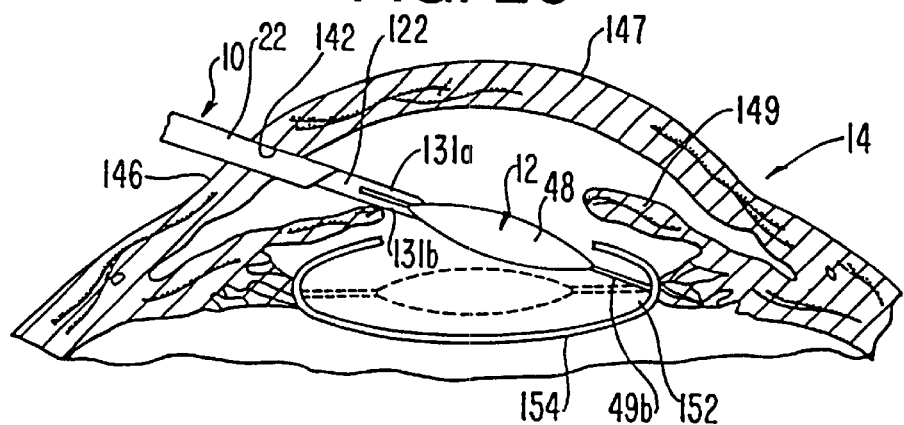
FIG. 26 is a cross sectional view of an eye illustrating the insertion and placement of an IOL.

The present invention pertains to a device 10 (FIG. 1) for inserting a flexible IOL 12 into an eye 14 of a patient (FIG. 26). The device comprises an outer tubular unit 16 and an inner plunger 18. In one embodiment, tubular unit 16 is formed by a base member 20, a cover 21 and a cannula 22 which are coupled together (FIGS. 1, 13 and 14). The components of device 10 may be composed of a plastic or metal material. For example, the components can be formed of polycarbonate or polypropylene. The plunger 18 and cannula 22 are preferably made of polypropylene. Nevertheless, a wide array of materials could be used.

Figure 5:
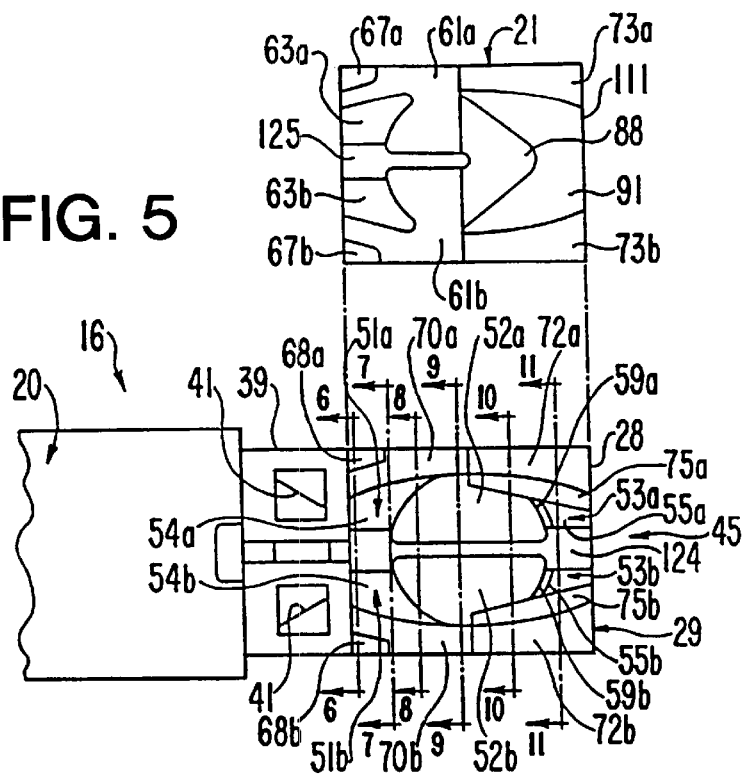
FIG. 5 is a partial top plan view of the tubular unit of the insertion device, including the staging area, with the cover removed and overturned, and the cannula omitted.
Figure 6:
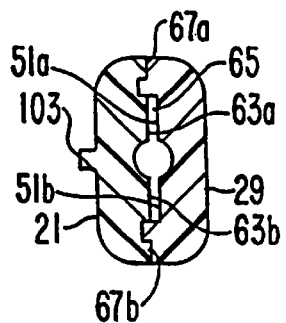
FIG. 6 is a cross sectional view taken along line 6—6 in FIG. 5 with the cover placed onto the shelf segment.
Figure 7:
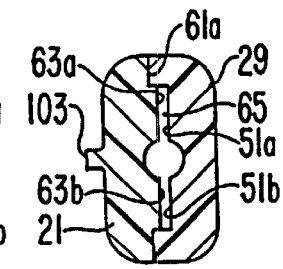
FIG. 7 is a cross sectional view taken along line 7—7 in FIG. 5 with the cover placed onto the shelf segment.
Figure 8:
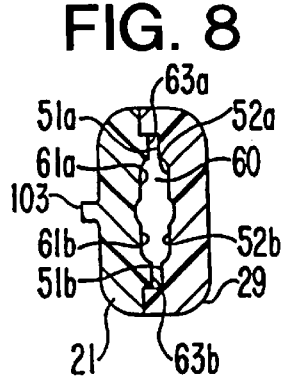
FIG. 8 is a cross sectional view taken along line 8—8 in FIG. 5 with the cover placed onto the shelf segment.
Figure 9:
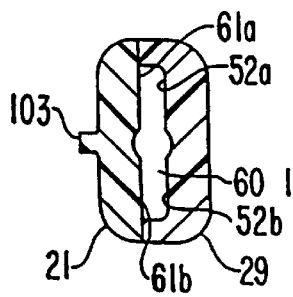
FIG. 9 is a cross sectional view taken along line 9—9 in FIG. 5 with the cover placed onto the shelf segment.
Figure 10:
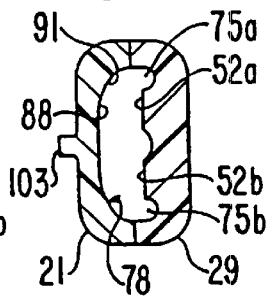
FIG. 10 is a cross sectional view taken along line 10—10 in FIG. 5 with the cover placed onto the shelf segment.
Figure 11:
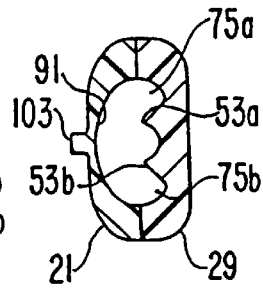
FIG. 11 is a cross sectional view taken along line 11—11 in FIG. 5 with the cover placed onto the shelf segment.
Figure 12:
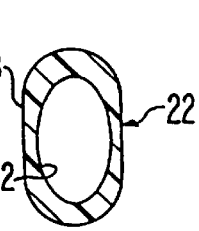
FIG. 12 is a cross sectional view taken along line 12—12 in FIG. 13.
Figure 15:
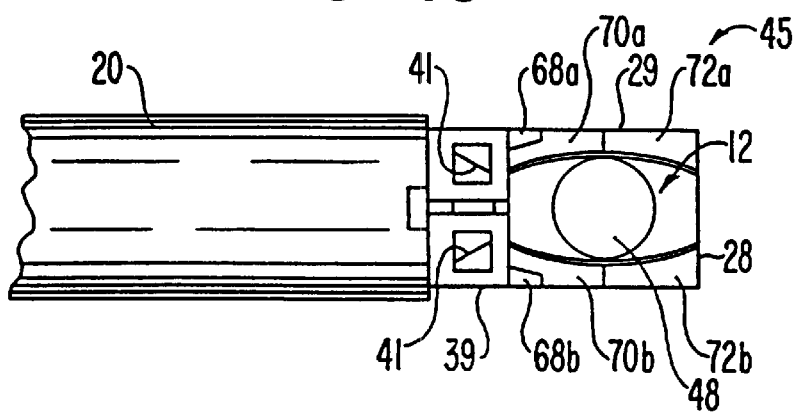
FIG. 15 is a partial top plan view of the tubular unit of the insertion device with an IOL in the staging area and with the cover and cannula omitted.
Figure 16:
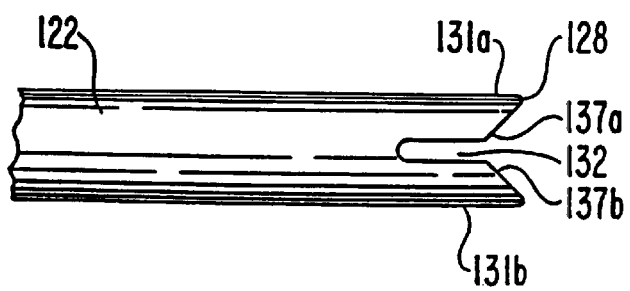
FIG. 16 is side elevational view of the distal tip of the plunger.
Figure 17:
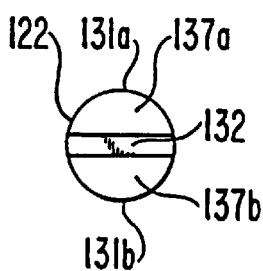
FIG. 17 is a front view of the distal end of the plunger.
Figure 18:
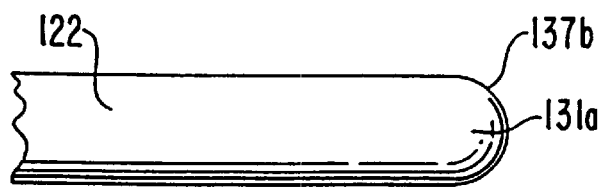
FIG. 18 is a top plan view of the distal end of the plunger.

Base member 20 is an elongate tubular member defining an inner passage 24 which is provided with a relatively large opening at proximal end 26 and an opening 27 of reduced size near, but spaced from, distal end 28 (FIGS. 1, 5, 13 and 14). A forwardly extending shelf segment 29 projects beyond opening 27 (FIGS. 5, 13 and 14). Base member 20 preferably has a generally oval cross sectional configuration, although other shapes could be used.

The inner passage 24 of base member 20 is adapted to movably receive therein plunger 18. A longitudinal groove 34 is preferentially positioned along one of the side walls 32 defining inner passage 24 (FIG. 13). Groove 34 cooperates with an extending flange 35 projecting laterally from plunger 18 to ensure that the plunger is properly oriented when fed into base member 20. Nevertheless, the groove construction could be replaced with a different structure for ensuring proper placement, such as forming at least a portion of inner passage 24 and plunger 18 with a D-shaped configuration. Near distal end 28, base member 20 forms a narrowed neck 39. Neck 39 defines distal opening 27 through which a portion of the plunger is passed to engage lens 12. Converging guideways 41 are positioned along opposite interior sides of passage 24 leading up to neck 39 (FIGS. 5, 13 and 14). Guideways 41 function to ease the passage of the plunger through neck 39 and over the shelf segment 29 for engagement with lens 12.

Figure 24:
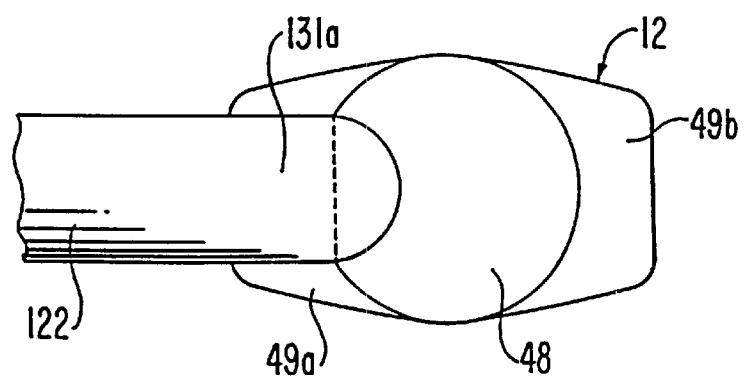
FIG. 24 is an enlarged top plan view of the distal tip of the plunger holding an IOL.

Shelf segment 29 is formed as an extension of roughly one half of the tubular base member 20. Shelf segment 29 cooperates with cover 21 to define a staging area compartment 45 for holding lens 12 (FIGS. 5–11 and 13–14). Lens 12 preferably has a central optic and a pair of adjacent web or plate haptics 49a, 49b (FIGS. 14 and 24). Nevertheless, other lens constructions, such as a lens with loop haptics, could also be used. The interior side of shelf segment 29 is formed in part by a pair of ledges 51a, 51b adjacent neck 39, a pair of recessed central flats 52a, 52b, and a pair of ramps 53a, 53b spaced forwardly of flats 52a, 52b (FIGS. 5–11 and 13–14). Ledges 51a, 51b and ramps 53a, 53b are each formed with top surfaces 54a, 54b, 55a, 55b to engage and support the haptics 49a, 49b of lens 12 in an initial unstressed position. Ramps 53a, 53b further include sloped surfaces 59a, 59b inclined to flats 52a, 52b. Flats 52a, 52b are recessed relative to top surfaces 54a, 54b, 55a, 55b to define a pocket 60 into which is received optic 48.

Cover 21 lies against shelf segment 29 to form staging area compartment 45 and enclose lens 12 in its initial unstressed position (FIG. 13). Cover 21 includes on its interior side recessed sections 61a, 61b, the central portions of which lie opposed to the proximal half of flats 52a, 52b. A pair of adjacent plateau segments 63a, 63b lie opposed to ledges 51a, 51b to define a gap 65 adapted to matingly receive and hold the proximal haptic 49a. Haptic 49a is loosely received in gap 65 so that it can be easily pushed out of staging area 45 during the insertion process. Ledges 51a, 51b, plateau segments 63a, 63b, and ramps 53a, 53b collectively support lens 12 by haptics 49a, 49b. In this initial position, optic 48 is held in suspension in pocket 60 so that the optic avoids contact with the interior walls of the staging area compartment 45.

The lens 12 can be installed in compartment 45 at a manufacturing plant and shipped to the user in device 10 with or without cannula 22 assembled in place. In this manner, device 10 can conveniently serve also as a lens package. Since lens 12 is supported in a generally suspended and unstressed state, the lens can be stored for a substantial length of time, perhaps as long as 10 years. Although the cover could be fixed to base member 20, it is designed for removal to enable inspection of the lens prior to its implantation in the eye. As shown in FIG. 14, cover 21 can be separable from base member 20, and secured in place by a snap fit, tape or other securing means. Nevertheless, the cover may be hinged to cannula 22, shelf segment 29, or neck 39.

Cover 21 includes projections 67a, 67b which mate with depressions 68a, 68b formed in shelf segment 29. In addition, shelf segment 29 includes proximal outer walls 70a, 70b and distal outer walls 72a, 72b. Proximal walls 70a, 70b abut the outer portions of recessed sections 61a, 61b. Distal walls 72a, 72b likewise abut walls 73a, 73b of cover 21. Distal walls 72a, 72b are preferably recessed relative to proximal walls 70a, 70b to enhance the mating fit of cover 21. During shipping of the device, the cover may be held closed by cannula 22, tape and/or other means to avoid inadvertent release of the lens.

Troughs 75a, 75b are formed in shelf segment 29 by extending the inner side wall surface 78 of compartment 45 downwardly between the outer distal sides of flats 52a, 52b and distal walls 72a, 72b. Troughs 75a, 75b are provided to receive the opposite sides of lens 12 as they are folded or curled along inner side wall surface 78. In the preferred embodiment, the troughs are deeper than flats 52a, 52b.

Cover 21 further includes a central, generally planar surface 88 inclined to extend away from shelf segment 29. A conically shaped portion 91 generally surrounding inclined surface 88 lies opposed to ramps 53a, 53b. These surfaces 88, 91 in cooperation with ramps 53a, 53b initiate the desired folding of the lens to its compressed state.

Cannula 22 is an elongate tubular member with an open proximal end 93 and an opposite open distal end 95 (FIGS. 1 and 12–14). Cannula 22 is preferably subdivided into three graduated sections 97–99. The proximal section 97 has a generally rectangular configuration and defines an inner cavity 101 sized to matingly receive the assembled shelf segment 29 and cover 21. Section 97 extends from distal end 28 to neck 39 of base member 20 and functions to hold cover 21 against shelf segment 29. An axial channel 102 is defined along one wall of cavity 101 to matingly receive ridge 103 extending up from cover 21. A hole 104 defined at the proximal end 93 of cannula 22 cooperates with a biased lock 106 on base member 20 to secure the cannula in place.

The medial section 98 of cannula 22 is significantly smaller than proximal section 97 so that a rim 110 is defined therebetween. Rim 110 acts as a shoulder in abutment with the aligned distal ends 28, 111 of base member 20 and cover 21. The inner wall of medial section 98 converges to define a funnel shaped passage 112. The funnel portion 112 preferably has an oval cross section, although other shapes could be used. This funnel section causes the lens to become substantially curled and compressed for entry into the eye.

The final, distal section 99 of cannula 22 is a long, narrow tube which defines an inner lumen 114. Distal section 99 is to be inserted through the narrow incision made in the eye. As with medial section 98, distal section 99 and lumen 114 preferably have an oval cross sectional shape. Of course, other shapes could be utilized if desired. To facilitate manufacturing and further compression of lens 12, lumen 114 is formed to taper slightly as it extends forward. Distal end 95 of cannula 22 is beveled to ease the insertion of the cannula into the incision and to assist in facilitating a gradual expansion of the lens as it exits from lumen 114.

Figure 27:
FIG. 27 is a perspective view of an alternative construction of the distal end of the cannula.
Figure 28:
FIG. 28 is a perspective view of a second alternative construction of the distal end of the cannula.
Figure 29:
FIG. 29 is a perspective view of a third alternative construction of the distal end of the cannula.
Figure 30:
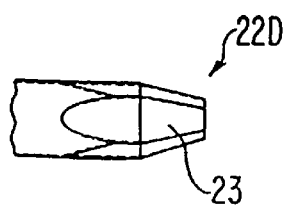
FIG. 30 is a side elevational view of a fourth alternative construction of the distal end of the cannula.
Figure 31:
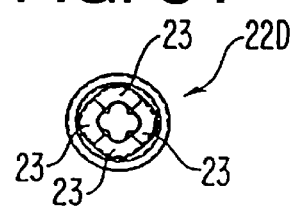
FIG. 31 is a front elevational view of the fourth alternative construction of the distal end of the cannula.

The distal section of the cannula may be provided with a wide variety of cross section configurations. As examples only, the cannula may be shaped with a clover-type tip 22A, a collapsible bag type tip 22B, or a wave-type tip 22C (FIGS. 27–29). These configured tips enhance the strength of the tip and thus permit a narrower construction to be used. The cannula tip may also be formed with a collet-like construction 22D. In this embodiment, the tip includes four separable leaves 23 which are expanded as the lens is pushed into the eye. The leaves 23 are biased to naturally close after the lens is placed into the eye and the plunger retracted.

Figure 37:
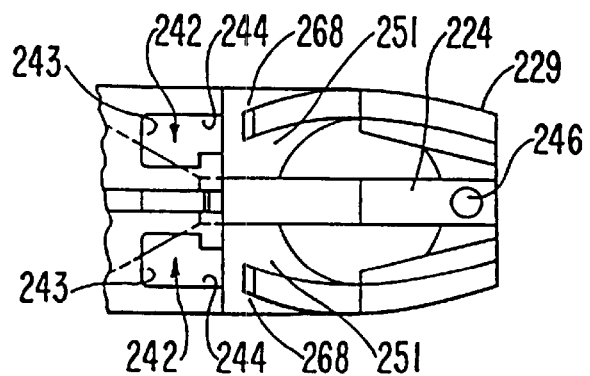
FIG. 37 is a plan view of the inside of the shelf segment of the alternative tubular unit embodiment of FIG. 34.

In the preferred embodiment, cover 221 is hinged to base member 220 of tubular unit 216 (FIGS. 34–37). The inside configuration of cover 221 is essentially the same as the inside configuration of cover 21, except that projections 267 are interconnected with plateau segments 263 by segments 264. Similarly, the inside configuration of shelf segment 229 is essentially the same as the inside configuration of shelf segment 29. As can be seen in FIG. 37, shelf segment 229 includes a corresponding interconnection of depressions 268 with ledges 251. Also, the central channel 224 of shelf segment 229, which accommodates passage of the plunger, is enlarged across its middle section. These modifications do not affect the operation of compressing and inserting the lens into an eye.

Also, as an optional feature, a hole 246 may be provided through shelf segment 229. The hole can be used to insert a viscoelastic material in embodiments wherein the cover is fixed to the shelf segment or otherwise not opened by the surgeon.

Cover 221 further includes a pair of rearwardly extending arms 265, which are provided with knobs 266 on their free ends. Arms 265 are provided to pivotally connect the cover to neck portion 239. Specifically, neck portion 239 includes a pair of sockets 242. Sockets 242 are formed to include substantially square shaped openings 243 (although other shapes could also be used) for receiving knobs 266, and channel portions 244 for receiving arms 265 when cover 221 is moved to its closed position (not shown). Recesses 245 are formed on the outside walls of openings 243 (FIG. 35) to receive the outward projection of knobs 266. Receipt of knobs 266 in recesses 245 functions to retain the cover 221 to base member 220.

Figure 32:
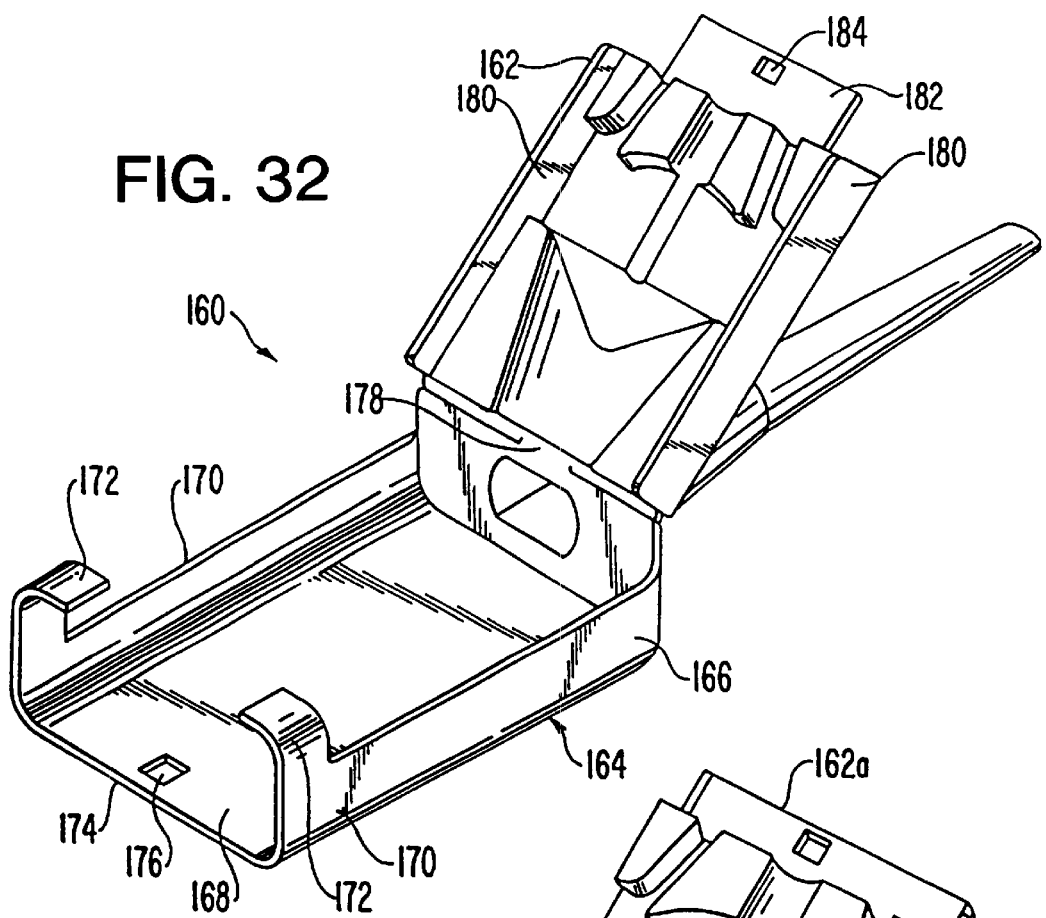
FIG. 32 is a perspective view of an alternative embodiment of the cannula.

In an alternative embodiment, cannula 160 includes a cover 162 hinged for movement between an open position and a closed position (FIG. 32). Cannula 160 has essentially the same construction as cannula 22, except for the incorporation of cover 162 in proximal section 164. Cover 162 has substantially the same construction as cover 21, including the same internal configuration for supporting and compressing the lens.

Proximal section 164 of cannula 160 comprises a base 166 and a cover 162. The base includes a bottom wall 168 and a pair of side walls 170 which extend upward only as high as shelf segment 29. The internal surfaces of bottom wall 168 and side walls 170 are shaped to matingly receive the external surface of shelf segment 29. A pair of upstanding flanges 172 are provided at proximal end 174 of base 166 to engage neck 39 and provide ample support for the cannula. A hole 176 is provided to cooperate with a protrusion (not shown) on shelf segment 29 in locking the cannula to the base member 20.

Cover 162 is movably connected to base 166 by a living hinge 178, although other hinge constructions could also be used. The cover is pivotally movable to an open position to permit inspection of the lens, and to a closed position for inserting the lens into a patient's eye. The lower edges of side walls 180 of the cover are formed to snap into a locking engagement with base 166 by any conventional construction (not shown); nevertheless, other fastening arrangements could be used. The internal configuration of cover 162 aligns with the internal configuration of shelf segment 29 in the same way as cover 21. Cover 162 further includes a proximal tab 182 which projects between flanges 172 to engage locking protrusion 106 in hole 184.

Figure 33:
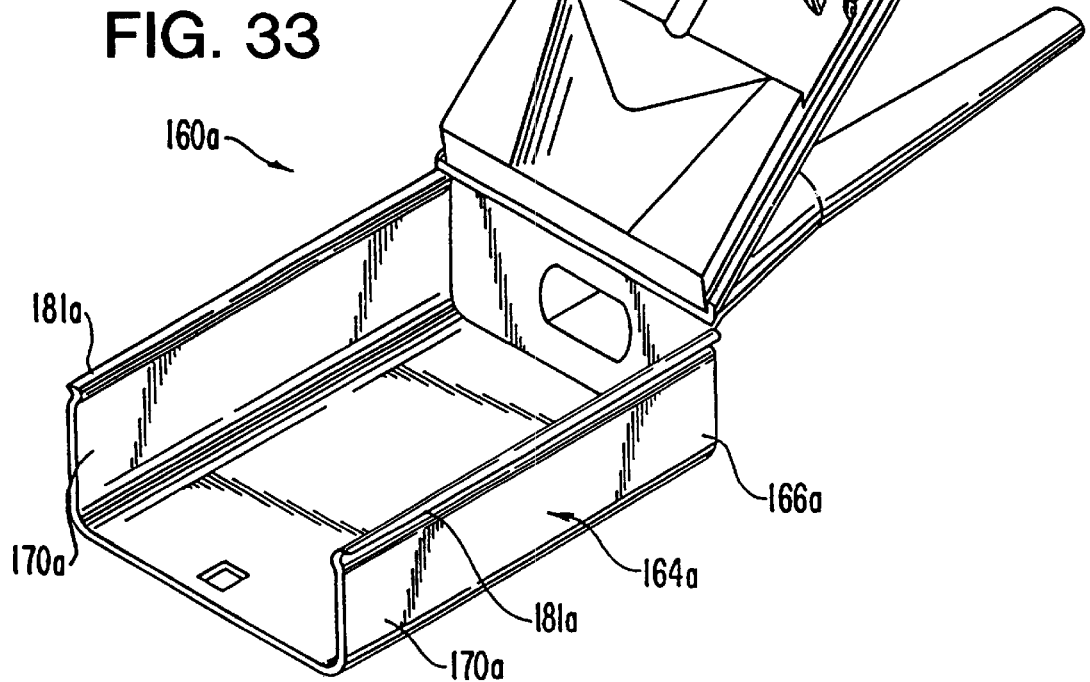
FIG. 33 is a perspective view of another alternative embodiment of the cannula.
Figure 34:
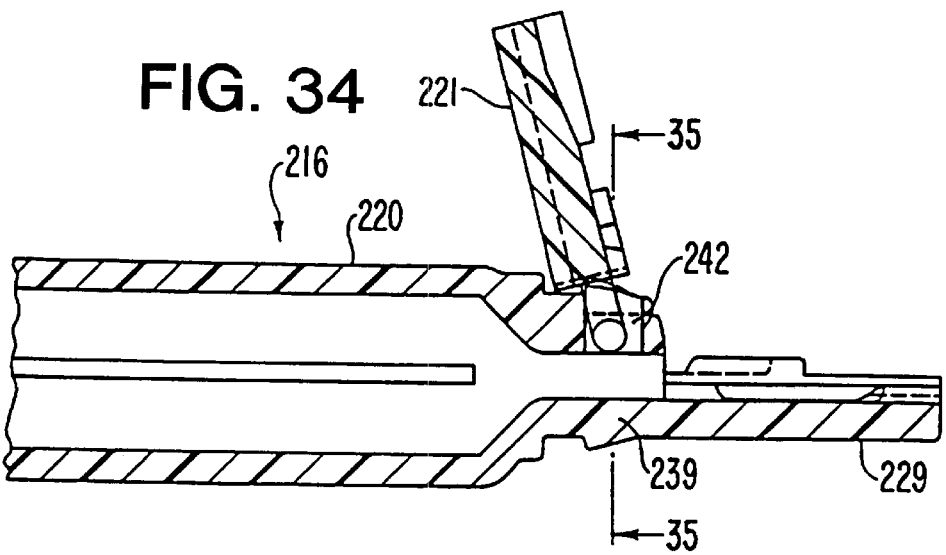
FIG. 34 is a partial, longitudinal cross sectional view of an alternative embodiment of the tubular unit with the cover open and the cannula removed.
Figure 35:
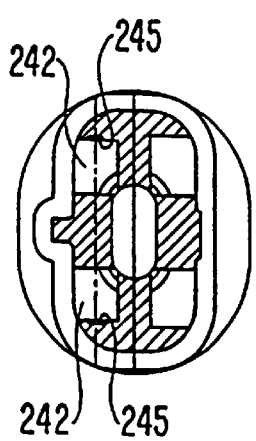
FIG. 35 is a cross sectional view taken along line 35—35 in FIG. 34, without the cover.
Figure 36:
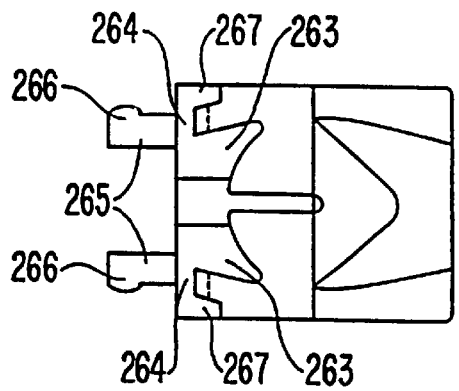
FIG. 36 is a plan view of the inside of the cover of the alternative tubular unit embodiment of FIG. 34.

As an alternative construction, side walls 170a of cannula 160a extend the entire depth of proximal section 164a, and cover 162a is provided with a flattened construction (FIG. 33). The internal side of cover 162a has the same configuration and relative positioning to shelf segment 29 as does the above-described cover 21. The edges 180a of cover 162a are preferably constructed to snap into locking engagement with edges 181b of side walls 170a. Nonetheless, other fastening arrangements could be used.

Preferably, cannula 162, 162a is composed of a polypropylene or other thermoplastic material. A disposable cover (not shown), can be used to ship and store the IOL in device 10. The disposable cover preferably has the same general size and shape as cover 162, 162a to enable it to snap into engagement with base 166, 166a. The disposable cover can have a wide variety of internal constructions so long as the IOL is adequately supported (as described above with respect to the other covers) and protected.

Figure 2:
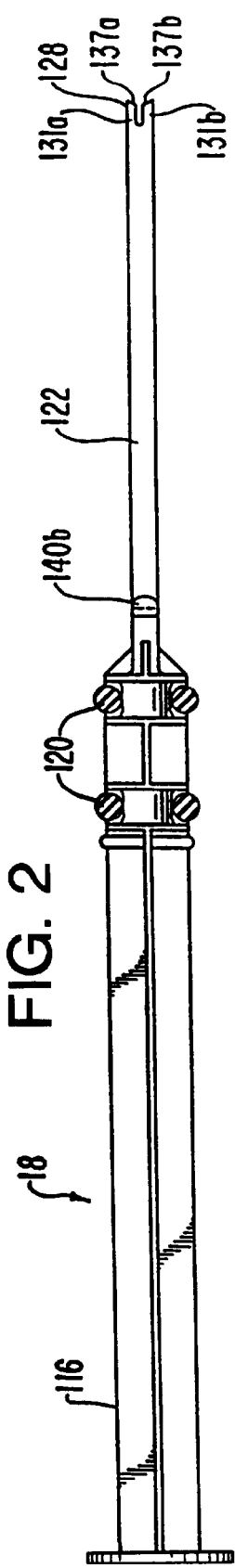
FIG. 2 is a side elevational view of the plunger of the insertion device.
Figure 3:
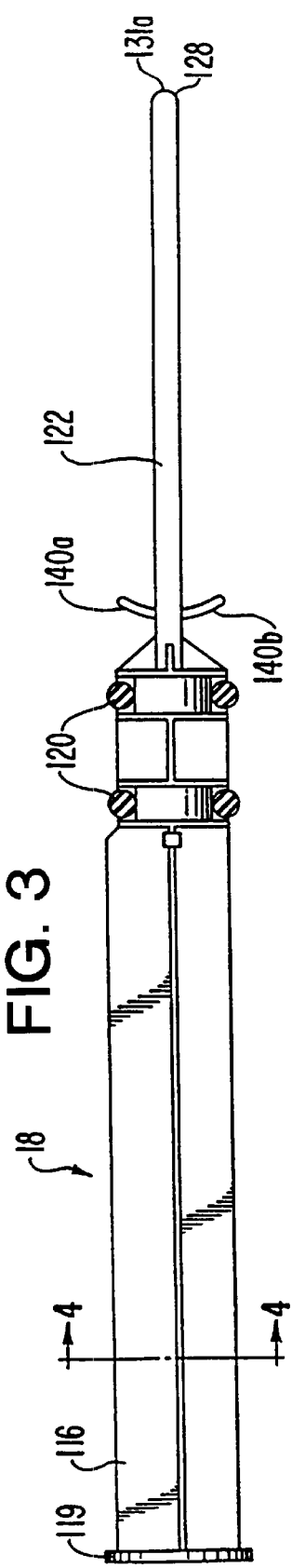
FIG. 3 is a top plan view of the plunger.
Figure 4:
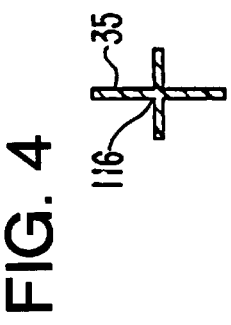
FIG. 4 is a cross sectional view taken along line 4—4 in FIG. 3.

Plunger 18 is an elongate member which is adapted to move through the inner passage 115 defined by tubular unit 16 (FIGS. 1 and 13). The plunger comprises a main body 116 preferably shaped with a cross shaped cross section (FIGS. 2–3). As discussed above, one flange 35 of the body is received into groove 34 to ensure proper placement of the plunger. A flat thumb pad 119 is provided on the proximal end of body 116 for manual operation of the device. Other constructions, however, may be provided to effect advancement of plunger 18 through tubular unit 16. The forward end of body 116 includes a pair of spaced apart O-rings 120*a*, 120*b*. The O-rings provide a level of resistance to enable a more controlled manual operation of the plunger. The O-rings further help to prevent the plunger from inadvertent movement when the surgeon manipulates device 10 during the surgical procedure. Other constructions, such as friction fit flanges, could be used in place of the O-ring.

Figure 25:
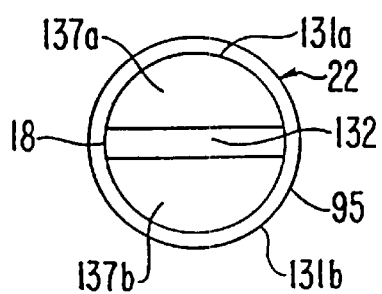
FIG. 25 is a front end view of the insertion device with the plunger extended to the distal end of the cannula.

A slender rod 122 projects forwardly beyond the main body 116 of plunger 18. The rod is intended to pass through staging area 45, funnel 112 and lumen 114. In order to provide sufficient clearance for rod 122, shelf segment 29 defines a channel 124 and cover 21 includes a relief 125 (FIGS. 5–11 and 13–14). Relief 125 only extends partway across cover 21 because surface 88 diverges away from the interior side of shelf segment 29 and thus provides sufficient clearance for rod 122. While rod 122 could have a wide range of shapes, it preferably has a circular or a slight ellipsoid shape adapted to pass through the distal end 95 of cannula 22 (FIG. 25).

The distal tip 128 of rod 122 is preferably bifurcated to define a pair of prongs 131*a*, 131*b* separated by a slot 132 (FIGS. 2–3, 16–18, 24 and 25). The slot is shaped to receive and hold proximal haptic 49*a* and optic 48 of lens 12. The ends 135*a*, 135*b* of prongs 131*a*, 131*b* are chamfered to form a pair of walls 137*a*, 137*b* which collectively form a generally V-shaped configuration. Depending on the sturdiness of the proximal haptic, walls 137*a*, 137*b* may or may not engage the proximal end of the optic 48. Prongs 131*a*, 131*b* are preferably identical to one another. Nevertheless, one prong 131*a* can be made narrower than the other prong 131*b* to allow extra space for the lens 12 to curl and compress during its passage through lumen 114 and into the patient's eye. Under ordinary circumstances, however, the extra space is not needed.

The distal tip of plunger 18 may alternatively be formed with other structural configurations which would hold the lens when the lens is pushed out of the cannula. For example, when implanting an IOL with loop shaped haptics, the plunger may be formed with a closed vertical slot (not shown) along the top of rod 122 in lieu of the open horizontal slot 132. In this arrangement, the lens would be positioned in staging area 45 with the haptics extending from points along the sides of the tubular unit. The haptic, which curls rearwardly would be inserted into the vertical slot when the lens is mounted in the staging area. To avoid inadvertent release of the haptic during shipping and storage, the plunger could be secured in a fixed position through the use of a latch, tape, or other securing means. In any event, the plunger would engage the optic portion of the lens with its distal tip, formed for example with only inclined surfaces like 137*a*, 137*b*. When the lens is initially extended beyond cannula 22, the noted haptic would remain entrapped in the slot which would not yet be exposed outside of cannula 22. When release of the lens is desired, the plunger can be pushed slightly farther to expose the vertical slot and free the trapped haptic. The plunger can then be retracted into the tubular unit 16 while the lens remains in the eye.

In one embodiment, a pair of resilient spring elements 140*a*, 140*b* extends laterally from rod 122 near the rod's proximal end (FIGS. 2–3). The spring elements function to press against guideways 41 when the free end 128 of rod 122 extends beyond cannula 22. This engagement with guideways 41 forces spring elements 140*a*, 140*b* to be pushed backward, and thereby create a biasing force to pull the plunger rearward into tubular unit 16. In the preferred construction, the spring elements (not shown) would extend forwardly, generally parallel with rod 122, from the front end of the main body. In this arrangement, the spring elements would be designed to curl inward upon engagement with guideways 141. Additionally, a coil spring (not shown) may be secured around the plunger/rod to provide the desired biasing force. Of course, other spring arrangements could also be used. The spring may also be omitted and the plunger retracted manually by the surgeon.

Figure 19:
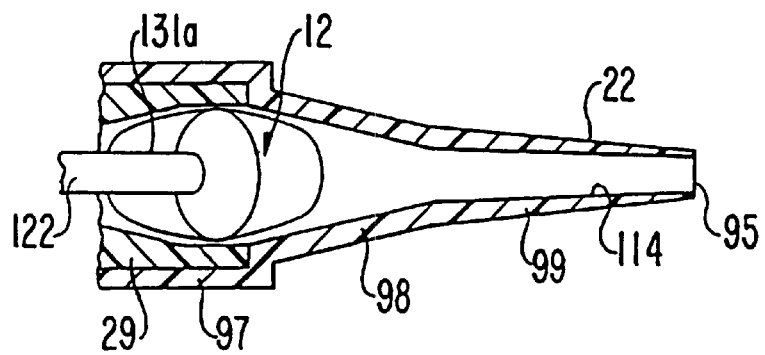
FIGS. 19–23 are each a schematic, partial cross sectional views taken along line 19—19 in FIG. 1, illustrating the movement of the plunger during insertion of the IOL into an eye.
Figure 20:
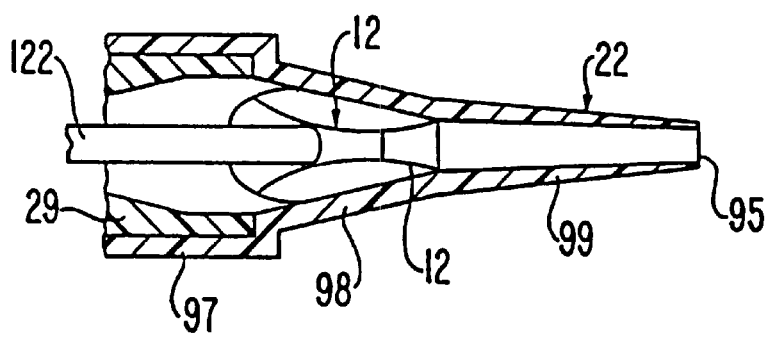
Figure 21:
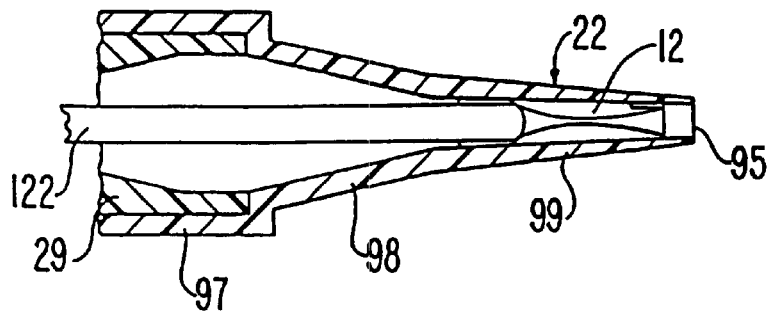

Once the lens has been inspected, device 10 can be assembled. A viscoelastic material, typically used for such surgical procedures, is placed in the cannula 22, typically prior to attachment of the cannula 22 to the assembly, as a lubricant for the insertion process. Once device 10 is assembled, the surgeon inserts the distal end of cannula 22 into the incision 142 in the eye 14. The surgeon then grasps lateral flanges 141 and pushes on pad 119 to move plunger 18 in a continuous forward motion. (FIG. 1). The continuous movement of rod 122 through tubular unit 16 engages lens 12 through its distal end 128 (FIG. 24). The proximal haptic 49*a* and possibly a portion of optic 48 are received into and held by slot 132, between walls 137*a*, 137*b*. The lens is then pushed forwardly by plunger 18 so that the distal side of optic 48 is shifted transversely toward cover 21 by sloped surfaces 59*a*, 59*b* of ramps 53*a*, 53*b*; that is, sloped surfaces 59*a*, 59*b* guide the central portion of optic 48 away from flats 52*a*, 52*b* (FIGS. 19 and 20). Inclined surface 88 and conical surface 91 provide ample clearance for this motion of the lens. As the center of the lens is shifted to move over ramps 53*a*, 53*b*, the sides of the lens are forced generally in the direction opposite to the ramps, by the inner wall surface 78 of cover 21. Specifically, the conical surface 91 in cover 21 causes lens 12 to curl into troughs 75*a*, 75*b*. Continued advancement of lens 12 through the tapering passage of tubular unit 16 causes continued curling and compression of the lens.

The lens continues its forward motion until plunger 18 pushes lens 12 beyond cannula 22. In the preferred construction, plunger 18 is pushed manually forward in a controlled manner, although other means, such as an electric motor or pneumatic drive, may be used.

Figure 22:
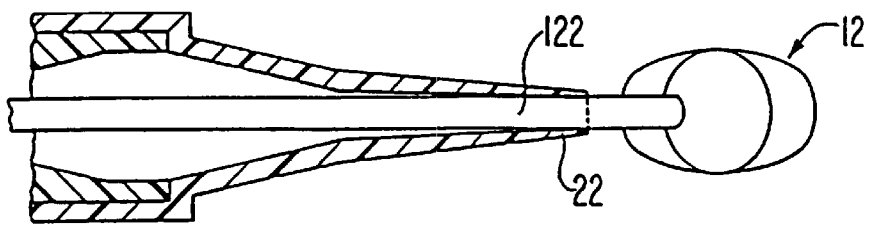
Figure 23:
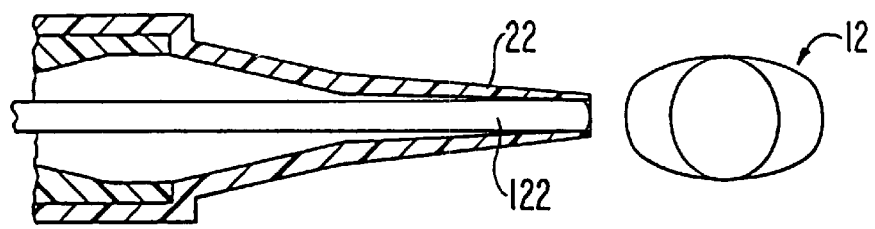

The leading haptic 49*b* is fed into the distal cul-de-sac 152 of the capsular bag 154. When lens 12 exits from cannula 22, it expands to its full unstressed state (FIGS. 22, 24 and 26). The lens, however, remains held in the slot 132 of plunger 18. Retention of the lens by the plunger reduces the risk of the lens expelling in an uncontrolled manner from the cannula and damaging the interior of the eye. Retaining the lens with the plunger also provides increased control in placing the lens in the eye. To release the lens, the plunger is retracted into tubular unit 16 so that the lens is pushed from slot 132 by distal end 95 of cannula 22 (FIG. 23). The retraction of plunger 18 is preferably performed automatically by biased spring elements 140*a*, 140*b* when pressure is released from thumb pad 119. A further implement, or perhaps device 10 itself, will typically be required to properly position the proximal haptic 49*a* into capsular bag 154.

The above-discussion concerns the preferred embodiments of the present invention. Various other embodiments as well as many changes and alterations may be made without departing from the spirit and broader aspects of the invention as described in the claims. For example, although the preferred embodiments concern the insertion of a flexible IOL into the eye, the invention is not so limited. The teachings of the present invention are applicable to the insertion of flexible membranes generally, including synthetic membranes, biopolymer membranes, and natural body tissues.

What is claimed is:

1. A device for inserting a flexible membrane into an eye, said device comprising:

a tubular member including a passage for receiving a flexible membrane, said passage having an open distal end for inserting the flexible membrane into an eye; and a plunger movably received within said passage of said tubular member for moving the flexible membrane through said open distal end of said tubular member and into the eye, said plunger including a distal tip with a forwardly opening slot having a fixed, narrow configuration dimensioned to continuously hold said flexible membrane to said plunger as the flexible membrane is pushed through said open distal end and after the flexible membrane is pushed entirely out of said passage, and said open distal end of said tubular member forming an abutment for releasing the continuously held flexible membrane from said slot when said distal tip is retracted into said passage, wherein said tubular member including a staging area along said passage for supporting the flexible membrane in a substantially unstressed state prior to be engaged by said plunger;

wherein said flexible membrane is a flexible intraocular lens having an optic portion and a haptic portion, and said staging area includes supporting surfaces for supporting said haptic portion of the lens so that the optic portion of the lens is suspended to avoid any substantial contact with interior portions of said tubular member in said substantially unstressed state; and wherein said supporting surfaces include a pair of distal supports and an open space adjacent each of said distal supports, said open spaces adapted to receive side portions of said lens as the lens is compressed.

2. A device in accordance with claim 1 in which said flexible membrane is a flexible intraocular lens having an optic and at least one haptic, and said plunger distal tip defines a slot for receiving and holding at least one haptic of the lens or the optic.

3. A device in accordance with claim 1 in which said passage of said tubular member tapers as it extends from said staging area to said distal end.

4. A device in accordance with claim 1 in which said staging area includes a cover which can be opened to expose the flexible membrane for inspection.

5. A device in accordance with claim 4 in which said tubular member further includes a separate cannula element which is received over said cover to hold said cover in a closed position.

6. A device in accordance with claim 1, in which said tubular member includes a cannula member and a base member, wherein said passage includes a staging area for supporting the flexible membrane, and said cannula member includes said open distal end, an open proximal end to receive the base member, and a cover which overlies said staging area, wherein said cover is hingedly connected to said cannula member for movement between an open position and a closed position.

7. A device in accordance with claim 6, which further includes a removable auxiliary cover, wherein said auxiliary cover overlies said staging area when storing the flexible membrane in said device, and said cover connected to said cannula overlies said staging area when inserting the flexible membrane into an eye.

8. A device for inserting a flexible intraocular lens, said device comprising:

a tubular member including a passage for receiving a flexible intraocular lens having an optic and at least one haptic, said passage having an open distal end for inserting the flexible lens into an eye; and a plunger movably received within said passage of said tubular member for moving the flexible lens through said open distal end of said tubular member and into the eye, said plunger including a distal tip having a slot for receiving and holding the lens, said slot including a proximal portion defined by a pair of generally parallel side walls for engaging a haptic of the lens and a distal portion defined by a pair of diverging sidewalls for engaging the optic of the lens, said slot being dimensioned for continuously holding said flexible lens to said plunger as the flexible lens is pushed through said open distal end and after the flexible lens is pushed entirely out of said passage.

9. A device for inserting a flexible membrane into an eye. said device comprising:

a tubular member including a passage for receiving a flexible membrane, said page having an open distal end for inserting the flexible membrane into an eye; and a plunger movably received within said passage of said tubular member for moving the flexible membrane through said open distal end of said tubular member and into the eye, said plunger including a distal tip with a holder dimensioned for continuously holding said flexible membrane to said plunger as the flexible membrane is pushed through said open distal end and after the flexible membrane is pushed entirely out of said passage, said plunger further including at least one spring element for retracting said plunger into said passage of said tubular member, wherein said spring element includes a pair of resilient projections which engage a wall surface in said passage to apply a biasing force to retract said plunger when said plunger extends outside of said distal end of said passage.

10. A device for inserting a flexible membrane into an eye, said device comprising:

a tubular member having a passage including a staging area for receiving a flexible membrane, an open distal end, and projection means for shifting a central portion of the flexible membrane transversely away from a side of said passage as the flexible membrane is advanced through said passage toward said open distal end to thereby control the direction of folding the flexible membrane; and a plunger movably received within said passage for moving the flexible membrane along said passage and into the eye.

11. A device in accordance with claim 10 in which at least a portion of said lumen tapers as it extends toward said distal end to compress said flexible membrane to a smaller configuration.

12. A device in accordance with claim 10 in which said flexible membrane is an intraocular lens having an optic portion and a haptic portion, and said staging area further includes means for supporting the haptic portion of the lens so that the optic portion of the lens is suspended in said passage to avoid any substantial contact with interior portions of said staging area.

13. A device in accordance with claim 10 in which said staging area includes a cover which can be opened to expose the flexible membrane in said unstressed state for inspection.

14. A device in accordance with claim 13 in which said tubular member further includes a separate cannula element which is received over said cover to hold said cover in a closed position.

15. A device in accordance with claim 13, which further includes a separate cannula element that includes said open distal end and said cover, wherein said cover is hingedly connected to said cannula element for movement between an open position and a closed position.

16. A device in accordance with claim 15, which further includes a removable auxiliary cover, wherein said auxiliary cover is mounted over said staging area when storing the flexible membrane in said device, and said cover of said cannula element is mounted in said staging area when inserting the flexible membrane into an eye.

17. A device in accordance to claim 10 in which said plunger includes means for holding said flexible membrane outside of said tubular member.

18. A device in accordance with claim 17 in which said plunger includes a distal tip and said holding means is comprised of a slot formed in said distal tip.

19. A device in accordance with claim 17 in which said plunger further includes a spring element for retracting said plunger into said passage of said tubular member.

20. A device for inserting a flexible membrane into an eye comprising:
a tubular member including a passage for receiving a flexible membrane, said passage having an open distal end for inserting the flexible membrane into an eye and a staging area for supporting the flexible membrane, an opening to facilitate loading and inspecting of the flexible membrane in the staging area, and a cover pivotally connected to said tubular member about an axis transverse to said passage for movement between an open position to permit access to the flexible membrane through said opening and a closed position to overlie said opening for insertion of the flexible membrane into an eye; and
a plunger movably received within said passage for moving the flexible membrane along said passage and into an eye,
wherein said cover includes at least one leg provided with an enlarged distal end, and said base includes at least one recess for rotatably receiving said enlarged distal end of said leg to effect pivotal movement of said cover.

21. A device in accordance with claim 20 in which said tubular member includes a base and a cannula, wherein said cannula is a separate member attachable to said base.

22. A device in accordance with claim 20, wherein said cover and said tubular member each include complimentarily-shaped hinging members such that said cover is releasably hinged to said tubular member about said axis transverse to said passage.

23. A method of inserting a flexible membrane into an eye, said method comprising placing a flexible membrane in a tubular member, compressing said flexible membrane so that the flexible membrane occupies a smaller cross-sectional area, inserting a distal portion of said tubular member through an incision in an eye, moving said compressed flexible membrane out of said tubular member and into the eye, holding the flexible membrane to the plunger in the eye after moving the flexible membrane out of the tubular member, selectively releasing the flexible membrane from the plunger, and retracting the tubular member from the eye, said releasing of the flexible membrane being effected by moving the plunger in a longitudinal direction and retracting said plunger into said tubular member so that the flexible membrane engages against the distal end of said tubular member to cause release of the flexible member from said plunger after the flexible membrane is moved out of said tubular member.

24. A method in accordance with claim 23, in which the flexible membrane is held in said tubular member such that a central portion thereof is suspended to avoid any substantial contact with interior portions of said tubular member.

25. A device for inserting a flexible membrane into an eye comprising:
a tubular member including a base, a cover, a cannula, a passage for receiving a flexible membrane, said passage having an open distal end in said cannula for inserting the flexible membrane into an eye and a staging area for supporting the flexible membrane, and an opening to facilitate loading and inspection of the flexible membrane in the staging area, said cover being pivotally attached to said base for movement between an open position to permit access to the flexible membrane through said opening and a closed position to overlie said opening for insertion of the flexible membrane into an eye, said cannula having a portion with a cavity which receives said cover and said base when said cover is in said closed position to retain the cover in the closed position; and
a plunger movably received within said passage for moving the flexible membrane along said passage and into an eye.

26. A device for inserting a flexible membrane into an eye comprising:
a tubular member including a base member, a cannula member, a passage for receiving a flexible membrane, said passage having an open distal end in said cannula for inserting the flexible membrane into an eye and a staging area for supporting the flexible membrane, an opening to facilitate loading and inspecting of the flexible membrane in the staging area, and a cover pivotally connected to the base member about an axis transverse to said passage for movement between an open position to permit access to the flexible membrane through said opening and a closed position to overlie said opening for insertion of the flexible membrane into an eye, said cannula member including a base portion having a cavity which is received over said cover and said base member to retain the cover in the closed position; and
a plunger movably received within said passage for moving the flexible membrane along said passage and into an eye.

27. A device for inserting a flexible membrane into an eye, said device comprising:
a tubular member including a passage for receiving a flexible membrane, said passage having an open distal end for inserting the flexible membrane into an eye and at least a portion which narrows toward said open distal end to compress the flexible membrane passed through said passage; and a plunger movably received within said passage to advance the flexible membrane through said passage and into the eye, said plunger including rotation prevention means for limiting the plunger solely to axial movement within the passage, and a holder to hold said flexible membrane to said plunger during advancement of the flexible membrane toward said open distal end and to provide means for limiting twisting of the flexible membrane so as to retain the flexible membrane in a proper orientation for insertion into the eye as the flexible membrane is advanced through at least a portion of said passage.

28. A device for inserting a flexible membrane into an eye comprising:

a tubular member including a passage for receiving a flexible membrane, said passage having an open distal end for inserting the flexible membrane into an eye and a staging area for supporting the flexible membrane, said tubular member having an opening to facilitate loading and inspection of the flexible membrane in the staging area and a pivotally attached cover for movement between an open position to permit access through said opening to the flexible membrane and a closed position to overlie said opening for insertion of the flexible membrane into an eye, one of said cover or said staging area having a protrusion and the other of said cover or said staging area having a recess to matingly receive said protrusion when said cover is moved to said closed position in order to properly align said cover with said staging area; and a plunger being movably received within said passage for moving the flexible membrane into an eye.

29. A device in accordance with claim 28 in which said cover and said staging area each include complimentary structures which cooperatively fold the lens as the lens is advanced in said passage toward said distal open end.

30. A method of inserting a flexible membrane into an eye, said method comprising:

placing a flexible membrane having a pair of opposite sides in a staging area of a passage of a tubular member so that the flexible membrane is supported in a generally unstressed state;

advancing the flexible membrane in the passage toward an open end of the passage;

using an internal structure of said passage to positively direct the flexible membrane against a predetermined wall of the passage having a generally concave shape as the flexible membrane is initially advanced in the passage so that the flexible membrane engages against and conforms generally to the concave shape of the passage wall and is formed into an arcuate configuration with one side of the flexible membrane facing the longitudinal axis of the passage with a generally concave shape while the flexible membrane is at least partially in said staging area;

advancing the flexible membrane engaged against the passage wall through a narrowing portion of the passage so that opposite edges of the concave side of the flexible membrane are folded inwardly toward one another;

inserting the open end of the passage into an eye;

advancing the folded flexible membrane through the open end and into the eye, and holding the flexible membrane to the plunger after the flexible membrane is pushed entirely out of the passage.

31. A method in accordance with claim 30 further comprising using a plunger to advance the flexible membrane in said passage, and holding the flexible membrane with the plunger to prevent undue twisting of the flexible membrane and thereby ensure that the flexible membrane is properly oriented when advanced into the eye.

* * * * *

UNITED STATES PATENT AND TRADEMARK OFFICE
CERTIFICATE OF CORRECTION

PATENT NO. : 6,336,932 B1  
DATED : January 8, 2002  
INVENTOR(S) : Dennis Alexander Figueroa et al.

It is certified that error appears in the above-identified patent and that said Letters Patent is hereby corrected as shown below:

Column 9,  
Line 33, "be" should read -- being --; and  
Lines 49 to 51, ", and said plunger distal tip defines a slot for receiving and holding at least one haptic of the lens or the optic" should be deleted.

Column 10,  
Line 29, "eye." should read -- eye, --;  
Line 32, "page" should read -- passage --.

Column 11,  
Line 9, "in said unstressed state" should be deleted;  
Line 25, "to" should read -- with --; and  
Line 61, "complimentarily-shaped" should read -- complementarily-shaped --.

Column 13,  
Line 37, "complimentary" should read -- complementary --.

Signed and Sealed this

Third Day of December, 2002

JAMES E. ROGAN  
*Director of the United States Patent and Trademark Office*